United States Patent

Jalink

[11] Patent Number: 6,080,950
[45] Date of Patent: Jun. 27, 2000

[54] METHOD FOR DETERMINING THE MATURITY AND QUALITY OF SEEDS AND AN APPARATUS FOR SORTING SEEDS

[75] Inventor: Hendrik Jalink, Dodewaard, Netherlands

[73] Assignee: Centrum Voor Plantenveredelings, Wageningen, Netherlands

[21] Appl. No.: 09/171,610

[22] PCT Filed: Apr. 28, 1997

[86] PCT No.: PCT/NL97/00230

§ 371 Date: Jan. 8, 1999

§ 102(e) Date: Jan. 8, 1999

[87] PCT Pub. No.: WO97/42489

PCT Pub. Date: Nov. 13, 1997

[30]     Foreign Application Priority Data

May 2, 1996  [NL]   Netherlands .......................... 1002984

[51] Int. Cl.⁷ ...................................................... B07C 5/00
[52] U.S. Cl. ........................ 209/577; 209/576; 209/587; 250/341.8; 250/341.3
[58] Field of Search ................................... 209/576, 577, 209/579, 588, 587, 938; 250/559.4, 341.8, 341.3

[56]               References Cited

U.S. PATENT DOCUMENTS

| | | | |
|---|---|---|---|
| 3,206,022 | 9/1965 | Roberts | 209/587 |
| 3,910,701 | 10/1975 | Henderson et al. | 356/39 |
| 4,084,905 | 4/1978 | Schreiber et al. | 356/85 |
| 4,204,950 | 5/1980 | Burford, Jr. | 209/577 |
| 4,350,442 | 9/1982 | Arild et al. | 209/587 |
| 4,586,613 | 5/1986 | Horii | 209/556 |
| 4,866,283 | 9/1989 | Hill, Jr. | 209/579 |
| 5,085,325 | 2/1992 | Jones et al. | 209/580 |
| 5,440,127 | 8/1995 | Squyres | 250/341.8 |
| 5,464,981 | 11/1995 | Squyres et al. | 250/341.8 |
| 5,791,497 | 8/1998 | Campbell et al. | 209/577 |
| 5,808,305 | 9/1998 | Leidecker et al. | 250/341.8 |
| 5,822,068 | 10/1998 | Beaudry et al. | 250/458.1 |

FOREIGN PATENT DOCUMENTS

| | | | |
|---|---|---|---|
| 0237363 | 9/1987 | European Pat. Off. | 21/64 |
| 0434644 | 6/1991 | European Pat. Off. | 21/64 |

OTHER PUBLICATIONS

Smilie, Robert, Applications fo Chlorophyll Fluorescence to the Postharvest Physiology and Storage of Mango and Banana Fruit and the Chilling Tolerance of Mango Cultivars, Asean Food Journal, vol. 3 No. 2 pp. 55–59, Jun. 1987.

Schmidt, Werner, Prompt and Delayed Fluorescence in Mature Tobacco Leaves: a Spectral Comparison, Photobiochemistry and Photobiophysics, vol. 9 pp. 89–97, 1985.

References B–M show the state of the art.

*Primary Examiner*—Donald P. Walsh
*Assistant Examiner*—David A. Jones
*Attorney, Agent, or Firm*—Ladas & Parry

[57]               ABSTRACT

The invention is related to a method and an apparatus for sorting seeds for the assessment of the maturity and quality of seeds by measuring the amount of chlorophyll fluorescence. Fluorescence of the chlorophyll molecule is induced by irradiating the seeds with electromagnetic radiation with a suitable wavelength and measuring the chlorophyll fluorescence. Properties of the method are the very high sensitivity, being fully non-destructive and the very high speed.

5 Claims, 2 Drawing Sheets

METHOD FOR DETERMINING THE MATURITY AND QUALITY OF SEEDS AND AN APPARATUS FOR SORTING SEEDS

The present invention refers to a method for determining the maturity and quality of seeds by irradiation with electromagnetic radiation. Due to this irradiation the chlorophyll present in the seeds will show prompt fluorescence. Furthermore, the invention refers to an apparatus for sorting the seeds essentially consisting of a feeder for the seeds, a part for the irradiation of the seeds with electromagnetic radiation, a part for measuring the signal reemitted from the seeds, and a separation part that works on basis of the signal reemitted from the seeds. Seeds being defined as the reproductive unit of the plant after sexual or non-sexual fertilization of the ovule. By chlorophyll all appearances of the chlorophyll molecule are meant, such as the known leaf-green chlorophyll, protochlorophyll, and all other possible configurations.

BACKGROUND OF THE INVENTION

Measuring the amount of chlorophyll fluorescence of the seed envelope is a good method for the assessment of the maturity and quality of seeds. It appeared that simultaneously with the maturation of the seed, the chlorophyll which is present in the seeds is broken down. Therefore, during the maturation process the amount of chlorophyll in the seed envelope decreases. Coincidently the colour changes from green (among others due to the presence of chlorophyll in the immature seeds) to a colour which is depending on the species being investigated. It also appeared that seeds with cracks in the seed envelope showed higher chlorophyll fluorescent signals. Due to these cracks in the seed envelope, the underlying chlorophyll containing tissue (cotyledons, endosperm or embryo) is uncovered. With equipment known and used for sorting seeds on colour, seeds can be sorted in green classes. However, the discrimination of maturity based on colour is not satisfactory: only large differences in maturity can be measured by colour sorting equipment. Therefore, the amount of chlorophyll of the seed envelope is a better basis to discriminate between seeds which differ in maturity.

With the assessment of the amount of chlorophyll fluorescence according to the invention, high certainty can be obtained on the maturity state of the seeds and whether cracks in the seed envelope are present. This makes it possible to sort the seeds with respect to their maturity and on the appearance of cracks in the seed envelope as described in the examples. The border of a class depends on the species and on the seedlot and is calculated on basis of the distribution of the measured fluorescence of a sample taken at random of the particular seedlot. The quality of the seeds in a class depends among others on the choice of the borders of the class. Generally speaking, regarding seeds which after maturation are located in a dry fruit (like seed of cabbage and carrot) the quality of mature seeds is higher compared to less mature or immature seeds. Seeds which maturate in a moist fruit (like seeds of pepper and tomato) have an optimum in their maturity. Immature seeds, but also seeds which are over-mature, have a lower quality compared to seeds of the optimal maturity. Quality being defined as the seed maturation stage, number and size of cracks in the seed envelope, germination percentage, speed of germination, uniformity of germination, vigour, percentage normal seedlings, health and storability. Seeds with an optimal and uniform maturity and without cracks germinate more uniform and give less abnormal seedlings. Seed treatments like priming have a greater effect (faster and more uniform germination) when the seeds have a certain maturity. Moreover, mature seeds have a better storability than less mature or immature seeds. Immature seeds and seeds with cracks are also more sensitive to infection by diseases. Furthermore, a negative health condition during the development of the seed can disturb the maturation process. This will result in unhealthy seeds with a lower degree of maturity than for healthy seeds.

A method to determine the amount of chlorophyll in seeds is known from the article of Tkachuk and Kuzina, in "Chlorophyll analysis of whole rapeseed kernels by near infrared reflectance", Canadian Journal of Plant Science (1982) 62: 875–884. They used a spectrophotometer to point a light beam of known wavelength onto the seed. After reflection the apparatus determines the fractional absorption of the light beam. Preferably the measurement is done in the 400–2400 nm wavelength range. The reflection spectrum is now a measure for the amount of chlorophyll. The amount of chlorophyll is determined with the aim to keep the amount of chlorophyll of the oil of the pressed seeds as low as possible. The main disadvantage of this method lies in the fact that different wavelengths have to be used, preferably 16, in order to obtain a reliable result. This method is not sensitive enough and too complicated to be used in sorting equipment.

In technology several other methods are known to predict the maturity and quality of moist fruit. S. Gunasekaran, M. R. Paulsen and G. C. Shove measured in "Optical Methods for Non-Destructive Quality Evaluation of Agricultural and Biological Materials", Review Paper, Journal of Agricultural Research (1985), 32, 209–241, the amount of chlorophyll in moist fruit to determine the maturity. They used the principle of light absorption at a wavelength of 670 nm. They do not mention the possibility of measuring the amount of chlorophyll of the seeds of a plant.

The method of light absorption is non-destructive with respect to the seeds which are being measured, but not suitable to sort seeds on the basis of the amount of chlorophyll, because of the low sensitivity.

R. M. Smillie, S. E. Hetherinton, R. N. Grantley, R. Chaplin and N. L. Wade measured in "Applications of chlorophyll fluorescence to postharvest physiology and storage of mango and banana fruit and the chilling tolerance of mango cultivars", Asean Food Journal (1987), 3(2), 55–59, the chlorophyll fluorescence with the intention to measure the photosynthetic activity of the fruit. They investigated the changes in chlorophyll fluorescence in the peel of harvested fruit during maturation or exposed to chilling. The speed at which the chlorophyll fluorescence decreased during chilling was used for selecting chilling resistant cultivars. The method of Smillie et al. takes at least 1 hour for the plant material to be dark adapted and then at least over a time period of two seconds the changes in chlorophyll fluorescence to follow, at low light conditions. They give several examples where chlorophyll fluorescence could be used. They do not mention the possibility of measuring the maturity and quality of seeds. They mention the possibility of measuring the 0-level fluorescence, F0, which is measured directly after the excitation light is turned on, but F0 depends on the photosynthesis. They claim that F0 does not have to correlate with the amount of chlorophyll. They also do not mention the possibility of measuring the prompt chlorophyll fluorescence of photosynthetically inactive chlorophyll in dry seeds and the application of sorting seeds with respect to the chlorophyll fluorescence signal on quality and maturity.

European patent application EP A 0 237 363 discloses a fluorescence measuring device designed to overcome the interference of reflectance in the fluorescence signal and not a device to measure the amount of chlorophyll in seeds with the intention to sort seeds. The present invention does not use the method of correcting for the reflectance of the sample according to claim 1 of EP A 0 237 363 but uses an interference filter with a LED-lamp or laser to prevent reflectance signals in the fluorescence signals.

European Patent Application EP-A 0 434 644 discloses a portable instrument designed to measure the ratio of fluorescence at 690 and 730 for the photosynthetic activity (as mentioned in claim 1 and 2) and to measure the Kautsky effect, which also is a response of photosynthetic activity. It does not mention the use of the instrument for measuring the chlorophyll fluorescence of photosynthetically inactive seeds and to sort seeds on their chlorophyll fluorescence signal on maturity and quality. Dry seeds show no photosynthetic activity and therefore no Kautsky effect.

There exists a destructive method to determine the amount of chlorophyll. This method, based on extraction, is internationally recognised as a standard procedure for the assessment of the amount of chlorophyll of rapeseed and is described by J. K. Daun in "Rapeseed—Determination of chlorophyll content—Spectrophotometric method", International Standard Organization, Geneva, (1992) ISO Method 10519. The method is based upon that dry seeds are ground by a mechanical grinder, whereupon the chlorophyll is extracted by a liquid. With a spectrophotometer in the same way as described by Tkachuk et al., but now in transmission, an absorption spectrum, which is characteristic for chlorophyll of the liquid, is made at three different wavelengths, 625, 665 and 705 nm. From this data the amount of chlorophyll can be calculated. The before mentioned method is clearly destructive since the seeds are ground. In the same way as with the article of Tkatchuk et al. also this method is used to determine the amount of chlorophyll to keep it as low as possible in the oil of the pressed seeds.

BRIEF SUMMARY OF THE INVENTION

The present invention is meant to give a method by which it is possible to sort seeds on maturity and quality on basis of their amount of chlorophyll in the seed envelope, without destroying the seed. Furthermore, it is possible to sort on cracks in the seed envelope based on the presence of chlorophyll in the inner tissue of the seed, which is uncovered due to the cracks. Characteristic for the invention is the very high sensitivity and the very high speed by which the amount of chlorophyll fluorescence of the seed envelope and of the inner tissue due to cracks can be determined. Furthermore, the invention is meant to give an apparatus by which seeds can be sorted on their maturity and quality with high accuracy and speed.

Accordingly the invention provides a method for determining the maturity and quality of seeds by irradiating same with electromagnetic radiation, characterized in that the electromagnetic radiation has such a wavelength that the chlorophyll which is present in the seed shows prompt fluorescence, which fluorescence is measured, whereby the measured fluorescence is not a measure for the photosynthetic activity.

DETAILED DESCRIPTION OF THE INVENTION

Figure 1:
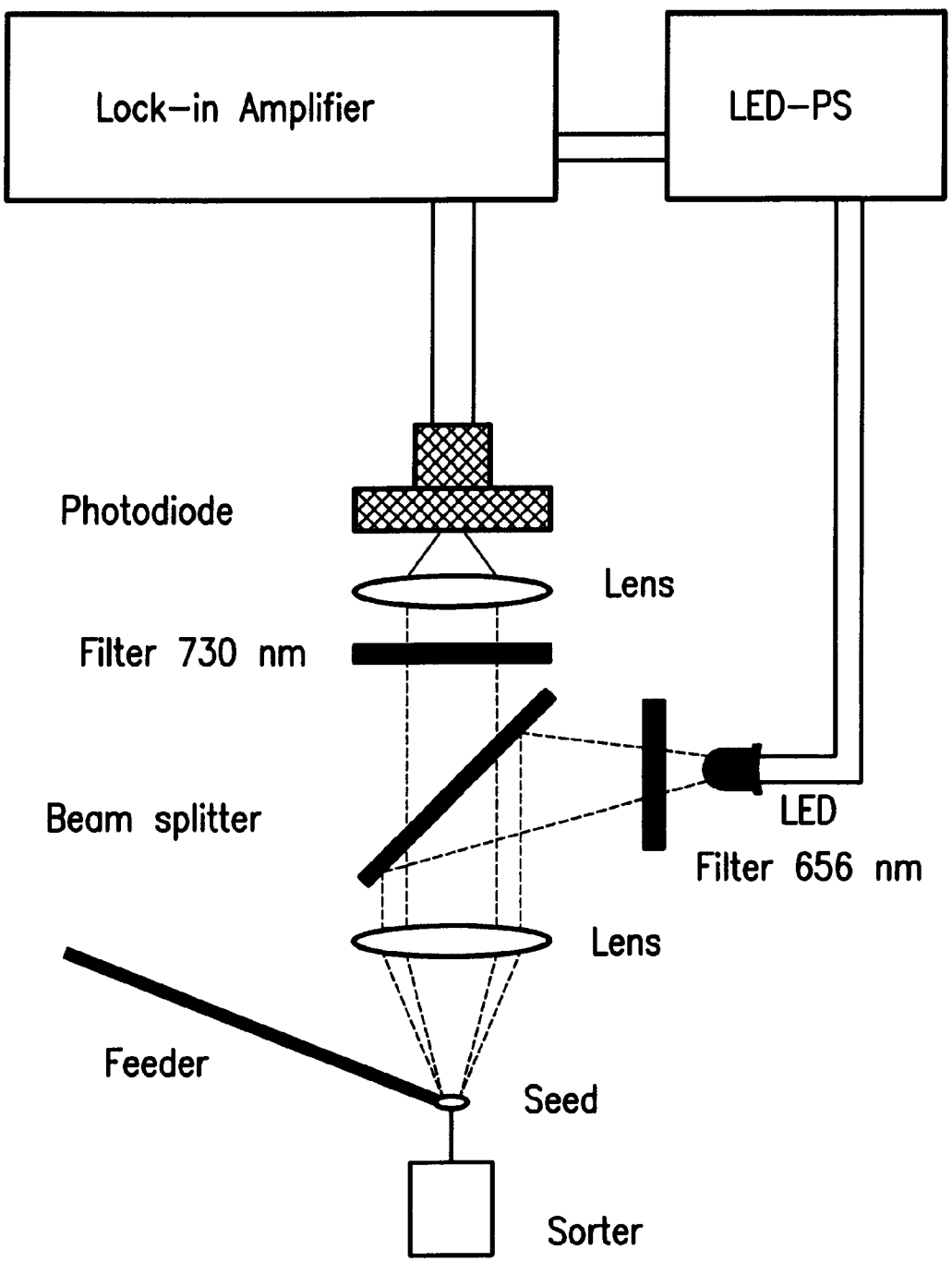
FIG. 1 shows an apparatus that can be used to carry out the method of the invention.

The method according to the present invention can be very well performed in an apparatus as mentioned herein before, with the feature that the electromagnetic radiation has such a wavelength that the chlorophyll which is present in the seed shows prompt fluorescence, which fluorescence is measured by the detector.

The present invention is based on a fluorescence measurement which is highly specific for chlorophyll. Other substances which influence the colour of the seed but do not fluoresce, will not interfere with the measurement. Moreover, with the invention small differences in the amount of chlorophyll of the seed envelope can be shown. This is because the fluorescence measurement is much more sensitive than a colour measurement.

Sorting on greenness and thus on the amount of chlorophyll of the seed envelope is difficult with a colour sorter. The accuracy of colour sorting normally fully depends on the accuracy of the measurement. With colour sorting, only seeds with a clear difference in greenness or large cracks in the seed envelope can be sorted. With a colour sorting apparatus it is not possible to discriminate between mature and immature seeds when the seeds have small or no differences in green levels and/or when the seeds have small cracks in the seed envelope. Seeds with low green levels and small cracks will therefore be classified as good. With a colour measurement of the greenness one can not suffice by measuring the absorption at 670 nm. A change in absorption around 670 nm can also be due to a change in the concentration of one or more other substances in the seed envelope which interact with the chlorophyll absorption signal around 670 nm. This is the reason why one has to use several wavelengths.

According to the invention, the difference in the amount of chlorophyll present in the seed envelope of individual seeds is directly demonstratable, and this is even possible in cases when the envelopes are completely uniform in colour for the human eye. Seeds of different maturity can have the same colour for the human eye, but different amounts of chlorophyll. This chlorophyll in the seed is photosynthetically inactive, because the metabolism of seeds stops after the drying process. Contrary to leaves and moist fruit, seeds show no so called "variable fluorescence" which is due to photosynthetic activity. The commonly used chlorophyll fluorescence equipment (e.g. the Pulse Amplitude Modulated fluorometer of U. Schreiber, described in "Detection of rapid induction kinetics with a new type of high frequency modulated chlorophyll fluorometer", Photosynthesis Research (1986) 9: 261–272) is designed to measure the photosynthetically active chlorophyll fluorescence. In literature no data is known about measuring the amount of chlorophyll fluorescence in relation to the maturity of seeds or the presence of cracks in the seed envelop. An appropriate method to measure chlorophyll is by means of irradiating the chlorophyll molecule with electromagnetic radiation, preferably blue or orange/red light, through which the chlorophyll molecule is electronically excited. The excited molecule loses its energy mainly by heat dissipation and by about 3% through emission of fluorescence, which is preferably measured in the far-red. Preferably the measurement is done in such a way that the irradiated electromagnetic radiation has a wavelength of about 435, 650 or 670 nm and the fluorescence is preferably measured at about 690 or 730 nm.

When according to the invention the intensity of the fluorescence is measured of each individual seed, the seeds can be sorted on their maturity and quality. Generally speaking, seeds with a high intensity of chlorophyll fluorescence are either immature or/and have cracks in the seed envelope.

Accordingly the invention further provides an apparatus for sorting seeds, essentially consisting of a feeder for the seeds, a part for the irradiation of the seeds with electromagnetic radiation, a detector area for measuring the signal reemitted from the seeds, and a separation part that works on basis of the signal reemitted from the seeds, characterized in that the electromagnetic radiation has such a wavelength that the chlorophyll present in the seed shows prompt fluorescence, which fluorescence is measured in the detector area.

The invention is very sensitive, completely non-destructive and very fast. These characteristics of the invention make it possible to construct a sorting device by which seeds can be selected on basis of the amount of chlorophyll fluorescence. Because the intensity of chlorophyll fluorescence is directly related to the maturity and the presence of cracks in the seed envelope and therefore the quality of the seed, it is now possible to sort seeds on their quality.

The method according to the invention can also be applied to sort seeds which are being used to extract oil. For the quality of oil which is extracted from seeds, it is important that the amount of chlorophyll is as low as possible. Chlorophyll reduces the oil quality and has to be removed out of the coil by certain extraction methods. With the present invention, seeds can be sorted based on the amount of chlorophyll, thereby only seeds with a low amount of chlorophyll are used to extract the oil.

For a good and constant quality of coffee the beans are sorted on their colour. This sorting has to be done when the beans are still moist. However, moist beans are more sensitive to deterioration than dry beans are. With the present invention coffee beans can be sorted based on the amount of chlorophyll after they have been dried. This makes it possible to dry the coffee beans directly after harvest, which means that there is less chance that the beans will deteriorate.

The present invention is suitable for the most types of seeds from horticultural crops, agricultural crops, ornamental crops, forestry crops and other seeds like nuts, kernels or beans. The invention works for all seeds of which the chlorophyll is broken down during the maturation process. Furthermore, the invention works for detecting cracks in the seed envelope of seeds of which the underlying tissue of the cracks contain chlorophyll.

It is preferable to perform a fluorescence measurement with the equipment as depicted in FIG. 1. This is a simple arrangement how the equipment can be constructed. The electromagnetic radiation can, among others, be induced by a LED or a laser. The light of for instance a LED, which is controlled by a LED power supply, has a maximum emission at 650 nm with a half bandwith of 22 nm and is filtered by a narrow filter at 656 nm with a half bandwith of 10 nm. The beam splitter reflects about 50% of the LED light towards the lens, which concentrates the light onto the seed. The chlorophyll fluorescence is captured by the same lens. With the filter it is certain that only fluorescence around 730 nm is detected by the photodiode. The lock-in amplifier modulates the LED light with a modulation depth of 100% and a duty cycle of 50% at a suitable frequency. Hereby the fluorescence is modulated with the same frequency. The alternating current of the photodiode is converted into a signal that is proportional to the intensity of the fluorescence. With the use of a laser as a radiation source the same is of course applicable.

It is further pointed out that it is now possible to apply the method in a handy portable instrument by which the distribution of the maturity of a sample of a seed lot can be measured for quality determination, for instance whether the seeds are good enough to be harvested. This can be done on the site where the seeds were grown. This does not have to be done anymore by eye or on "feeling" or at a fixed time after pollination. Due to weather influences it can occur that it is necessary to harvest earlier or later.

The invention can also be applied in seed sorting equipment. The invention can be built in all kinds of sorting equipment. The invention is especially applicable in the known colour sorting devices. The light source can be replaced by the electromagnetic radiation source (for instance a LED or a laser) and the colour meter by a photodiode.

The invention will now be demonstrated by several examples.

EXAMPLES

In the next examples the chlorophyll fluorescence of the seed envelope of every individual seed was measured according to the invention. Tests were being carried out with white cabbage seeds (*Brassica oleracea*), sugarbeet seeds (*Beta vulgaris*), polished sugarbeet seeds (*Beta vulgaris*), disinfected carrot seeds (*Daucus carota*), pepper seeds (*Capsicum annuum*) and tomato seeds (*Lycopersicon esculentum*). With the described invention improvements were obtained in the germination of seeds and the usable transplants, i.e. the number of seedlings that grow out to normal plants.

Example 1

With the present invention the chlorophyll fluorescence of 1500 white cabbage seeds (*Brassica oleracea*) cv. 'Bartolo F1' was individually measured and separated on basis of the distribution of the fluorescence into 2 classes. The distribution of the 2 classes is given in table 1. The germination tests were carried out by imbibing the seeds on moist filter paper on a petri dish at a temperature of 20° C. and covered with a transparent lid for 12 hours in the dark and 12 hours in the light. The seeds were visually inspected on the emergence of the root tip (table 1), whereupon the speed of germination, $t_{50}$, was calculated. After 5 and 10 days the seedlings were evaluated according to the standard rules of ISTA as described in "International Rules for Seed Testing 1993", Seed Science and Technology 21, 1993 (table 1). The seeds in the class of low fluorescence germinated at 100%, with 98% normal seedlings compared to 68% and 24%, respectively for the high class. The improvement of the low class as compared to the control is small, since the high class exists of only 1.8% of the original population. The results show that commercial available Brassica seed of very high quality, could be improved and that the seeds of low quality were selected, although this was a small fraction of the seed lot. The germination could be improved from 99.4% of the control to 100% and the normal seedlings from 96.7 to 98%.

TABLE 1

Quality of white cabbage seeds before sorting (control) and after sorting in 2 classes with the use of chlorophyll fluorescence

| chlorophyll fluorescence | low | high | control |
|---|---|---|---|
| distribution (%) | 98.2 | 1.8 | 100 |
| germinated seeds (%) | 100 | 68 | 99.4 |
| normal seedlings (%) | 98 | 24 | 96.7 |
| $t_{50}$ (days) | 2.24 | 2.18 | 2.23 |

Example 2

The test was carried out in the same way as described in example 1, but now for 700 white cabbage seeds (*Brassica oleracea*) cv. 'Megaton F1'. The seeds in the low and high class gave equal germination of 100%, while the low class gave an improvement of the percentage of normal seedlings. The speed of germination of both the high and low class were almost equal. The improvement of this seedlot of very high quality does not show from the direct germination data, but comes from the improvement of the appearance of the seedlings. Of the low class only 8% had yellow spots on their cotyledons, while for the high class this amounted 26%. The results show that also for Brassica seed of very high quality after selection the quality could be improved.

TABLE 2

Quality of white cabbage seeds before sorting (control) and after sorting in 2 classes with the use of chlorophyll fluorescence

| chlorophyll fluorescence | low | high | control |
|---|---|---|---|
| distribution (%) | 92.6 | 7.4 | 100 |
| germinated seeds (%) | 100 | 100 | 100 |
| normal seedlings (%) | 99.5 | 96 | 99.2 |
| $t_{50}$ (days) | 1.35 | 1.38 | 1.36 |
| deviated cotyledons (%) | 8 | 26 | 9.3 |

Example 3

This test was carried out the same way as described in example 1, but now for 700 white cabbage seeds (*Brassica oleracea*) cv. 'Transam F1'. The seeds in the class with low chlorophyll fluorescence resulted in a germination of 99%, while the germination of the high class scored 68%. There was also a large difference in the normal seedlings between the low and high class, 88 compared to 48%. There also was an improvement in the speed of germination between the low and high class. The results show that also for this cultivar of Brassica seed the quality could be improved based on the selection on the amount of chlorophyll fluorescence.

TABLE 3

Quality of white cabbage seeds before sorting (control) and after sorting in 2 classes with the use of chlorophyll fluorescence

| chlorophyll fluorescence | low | high | control |
|---|---|---|---|
| distribution (%) | 92.7 | 7.3 | 100 |
| germinated seeds (%) | 99 | 64 | 96.7 |

TABLE 3-continued

Quality of white cabbage seeds before sorting (control) and after sorting in 2 classes with the use of chlorophyll fluorescence

| chlorophyll fluorescence | low | high | control |
|---|---|---|---|
| normal seedlings (%) | 88 | 48 | 85.1 |
| $t_{50}$ (days) | 1.68 | 1.97 | 1.69 |

Example 4

This test was carried out in the same way as described in example 1, but now for 1180 white cabbage seeds (*Brassica oleracea*) separated into 4 classes. The seeds in the class with very low fluorescence resulted in a germination of 100% and all normal seedlings. The speed of germination of this class was much better than the other classes and for the control. There is a negative correlation between the amount of chlorophyll fluorescence and the percentage of seedlings and a positive correlation between the amount of chlorophyll fluorescence and the speed of germination. The quality of the seeds increases with decreasing relative amount of chlorophyll. The results show that the quality of commercial Brassica seed could be improved. The germination of the control could be improved from 95.6 to 100% and the percentage of normal seedlings from 89.7 to 100%.

TABLE 4

Quality of white cabbage seeds before sorting (control) and after sorting in 4 classes with the use of chlorophyll fluorescence

| chlorophyll fluorescence | very low | low | high | very high | control |
|---|---|---|---|---|---|
| distribution (%) | 41.9 | 30.1 | 14.8 | 13.2 | 100 |
| germinated seeds (%) | 100 | 100 | 97 | 70 | 95.6 |
| normal seedlings (%) | 100 | 96 | 90 | 42 | 89.7 |
| $t_{50}$ (days) | 1.34 | 1.47 | 1.72 | 2.82 | 1.41 |

Example 5

With the present invention the chlorophyll fluorescence of 500 sugarbeet seeds (*Beta vulgaris*) was individually measured and subsequently separated on basis of the distribution of the fluorescence into 2 classes. The distribution of the 2 classes is given in table 5. The difference with the cabbage seeds of the preceding examples is that sugarbeet seeds are encapsulated in an envelope of which the chlorophyll fluorescence was measured. The germination tests were carried out by first disinfecting the seeds with thiram, after that four hours of rinsing with tap water at 25° C. and drying back at the same temperature. Next the seeds were placed between moisted plated filter paper in plastic trays in a germination cabinet at a temperature of 20° C. in the dark. The seeds were visually inspected on the emergence of root tips, whereupon the speed of germination, $t_{50}$, was calculated (table 5). After 7 and 14 days the seedlings were evaluated according to the standard ISTA rules as described in "International Rules for Seed Testing 1993", Seed Science and Technology 21, 1993 (table 5). The seeds in the class of low fluorescence resulted in a germination of 97.5%, while the germination of the high class was 90%. Furthermore, there was a large difference between the percentage of normal seedlings of the low and high class, 95% and 86%, respectively. The speed of germination of the low and high class were equal. The results show that also for sugarbeet seed, whereby the chlorophyll fluorescence was measured of the envelope of the sugarbeet seed, the quality by sorting could be improved.

TABLE 5

Quality of sugar beet seeds before sorting (control) and after sorting in 2 classes with the use of chlorophyll fluorescence

| chlorophyll fluorescence | low | high | control |
|---|---|---|---|
| distribution (%) | 79.6 | 20.4 | 100 |
| germinated seeds (%) | 97.5 | 90 | 96 |
| normal seedlings (%) | 95 | 86 | 93 |
| $t_{50}$ (days) | 2.76 | 2.76 | 2.76 |

Example 6

This test was carried out in the same way as described in example 5 for 900 sugarbeet seeds (*Beta vulgaris*) with the difference that these seeds were polished. The choice of the classes was the same as in example 5. The seeds in the class with low fluorescence resulted in a germination of 98%, while the germination of the high class was 92%. There was also a distinctive difference between the percentage normal seedlings of the low and high class, 97 and 90%, respectively. The speed of germination of the two classes were almost equal. The results show that also for polished sugarbeet seeds the quality after sorting could be increased.

TABLE 6

Quality of polished sugar beet before sorting (control) and after sorting in 2 classes with the use of chlorophyll fluorescence

| chlorophyll fluorescence | low | high | control |
|---|---|---|---|
| distribution (%) | 88.9 | 11.1 | 100 |
| germinated seeds (%) | 98 | 92 | 97.3 |
| normal seedlings (%) | 97 | 90 | 96.2 |
| $t_{50}$ (days) | 2.40 | 2.45 | 2.43 |

Example 7

With the present invention the chlorophyll fluorescence of the envelope of 700 carrot seeds (*Daucus carota*) cv. 'Amsterdam' was individually measured and subsequently the seeds were sorted on basis of the distribution of the fluorescence into 2 classes. The distribution of the 2 classes is given in table 7. The main difference with the preceding examples was that these seeds were disinfected with thiram, which gave them an orange colour. The germination tests were carried out by first submerging the seeds in water for three days at a temperature of 10° C. Next the seeds were placed on moist filter paper in plastic trays in a germination cabinet at an alternating temperature of 20° C.–30° C., at 20° C. in the dark (16 hours) and at 30° C. in the light (8 hours). The seeds were visually inspected on the emergence of the root tip, whereupon the speed of germination, $t_{50}$, was calculated (table 7). After 7 and 14 days the seedlings were evaluated according to the standard ISTA rules as described in "International Rules for Seed Testing 1993", Seed Science and Technology 21, 1993 (table 5). The seeds in the class with low fluorescence resulted in a germination of 97%, while the germination of the high class scored 91%. There was also an improvement of the percentage of normal seedlings of the low class with respect to the high class, 95 and 86%, respectively. It was also observed that according to the speed of germination the seeds of the low class were of better quality than of the high class. The results show that the invention also gives improvements on carrot seed that has been treated with a disinfectant.

TABLE 7

Quality of disinfected (thiram) carrot seeds before sorting (control) and after sorting in 2 classes with the use of chlorophyll fluorescence

| chlorophyll fluorescence | low | high | control |
|---|---|---|---|
| distribution (%) | 70.7 | 29.3 | 100 |
| germinated seeds (%) | 97 | 91 | 95.2 |
| normal seedlings (%) | 95 | 86 | 92.4 |
| $t_{50}$ (days) | 1.51 | 1.70 | 1.55 |

Example 8

With the present invention the chlorophyll fluorescence of 500 pepper seeds (*Capsicum annuum*) cv. 'Flair F1' was individually measured and subsequently the seeds were sorted on basis of the distribution of the fluorescence into 2 classes. The distribution of the 2 classes is given in table 8. The germination tests were carried out in a solution of water with 0.2% $KNO_3$ moisted filter paper in plastic trays in a germination cabinet at an alternating temperature of 20° C.–30° C., at 20° C. in the dark (16 hours) and at 30° C. in the light (8 hours). The seeds and seedlings were evaluated the same way as described in example 7. The difference with the seeds from the preceding examples is that pepper seeds are surrounded by a fruit that is still moist after the seeds are mature. Contrary, the preceding examples where the fruit which surrounds the seeds, dries out and the seeds in the dry state are physiologically inactive. Due to the moist environment pepper seeds can be physiologically active. If pepper seeds are not dried at the right time after being fully mature, they can deteriorate in quality. The seeds in the class with low fluorescence gave a germination of 99.5%, while the germination of the high class was 100%. There also was a small difference in the percentage of normal seedlings of the low and high class, 96 and 98%, respectively. The difference in the speed of germination of the two classes was very small. It was observed that the health of the seeds from the high class was better as compared to the low class: 2.5 and 27% infection (Alternaria) on the seed coat, respectively. With the choice of the classes it is probably the case that the high class is of better quality than the low class. This is probably caused by the fact that the change of an infection by microflora increases as the seeds are for a longer time in a moist environment, the fruit. The germination results show that the two classes were already fully mature, but that due to prolonged maturation the probability on infection increases.

TABLE 8

Quality of pepper seeds before sorting (control) and after sorting in 2 classes with the use of chlorophyll fluorescence

| chlorophyll fluorescence | low | high | control |
|---|---|---|---|
| distribution (%) | 54.8 | 45.2 | 100 |
| germinated seeds (%) | 99.5 | 100 | 99.7 |
| normal seedlings (%) | 96 | 98 | 96.9 |
| $t_{50}$ (days) | 3.99 | 4.27 | 4.06 |
| infected (%) | 27 | 2.5 | 15.9 |

Example 9

This test was carried out in the same way as in example 8 but now for 600 pepper seeds (*Capsicum annuum*) cv.

'Kelvin F1' sorted into 3 classes after the chlorophyll fluorescence was measured. The seeds in the class with low fluorescence resulted in a germination of 98%, while the germination of the middle and high class was 100%. There was also an improvement in the percentage of normal seedlings: 100, 97.5 and 92% for the high, middle and low class, respectively. At none of the classes infections were observed. With the sorting of the seeds in the 3 classes it appeared that the low class was of a lower quality than the middle and the high class was a little bit better in quality than the middle class. Seeds of these two classes were almost of the same quality.

TABLE 9

Quality of pepper seeds before sorting (control) and after sorting in 3 classes with the use of chlorophyll fluorescence

| chlorophyll fluorescence | low | middle | high | control |
| --- | --- | --- | --- | --- |
| distribution (%) | 11.7 | 79.8 | 8.5 | 100 |
| germinated seeds (%) | 98 | 100 | 100 | 99.8 |
| normal seedlings (%) | 92 | 97.5 | 100 | 97.1 |
| $t_{50}$ (days) | 3.92 | 3.97 | 4.05 | 3.97 |

Example 10

With the present invention the chlorophyll fluorescence of 500 tomato seeds (*Lycopersicon esculentum*) cv. 'Tanaki' was individually measured and sorted on basis of the distribution of the fluorescence into 3 classes. The distribution of the 3 classes is given in table 10. The germination tests were carried out in a solution of water with 0.2% $KNO_3$ moisted filter paper in plastic trays in a germination cabinet at an alternating temperature of 20° C.–30° C., at 20° C. in the dark (16 hours) and at 30° C. in the light (8 hours). The seeds and seedlings were evaluated and the speed of germination, $t_{50}$, was calculated as described in example 7. Just like pepper seeds, tomato seeds are after being mature in a moist fruit. After being fully mature the quality of tomato seeds can decrease if they are not dried at the right moment. From the table it appears that the middle class contains seeds with the highest quality. This results from the speed of germination and normal seedlings. The low class was of a low quality and the quality of the high class was even lower. From the results it can be concluded that with the invention classes could made, whereby the quality of the tomato seeds of the middle class was the highest and could be improved as compared to the control.

TABLE 10

Quality of tomato seeds before sorting (control) and after sorting in 3 classes with the use of chlorophyll fluorescence

| chlorophyll fluorescence | low | middle | high | control |
| --- | --- | --- | --- | --- |
| distribution (%) | 13.4 | 74.8 | 11.8 | 100 |
| germinated seeds (%) | 100 | 99.5 | 96 | 99.2 |
| normal seedlings (%) | 94 | 97.5 | 84 | 95.4 |
| $t_{50}$ (days) | 4.02 | 3.72 | 4.35 | 3.79 |

Example 11

Figure 2:
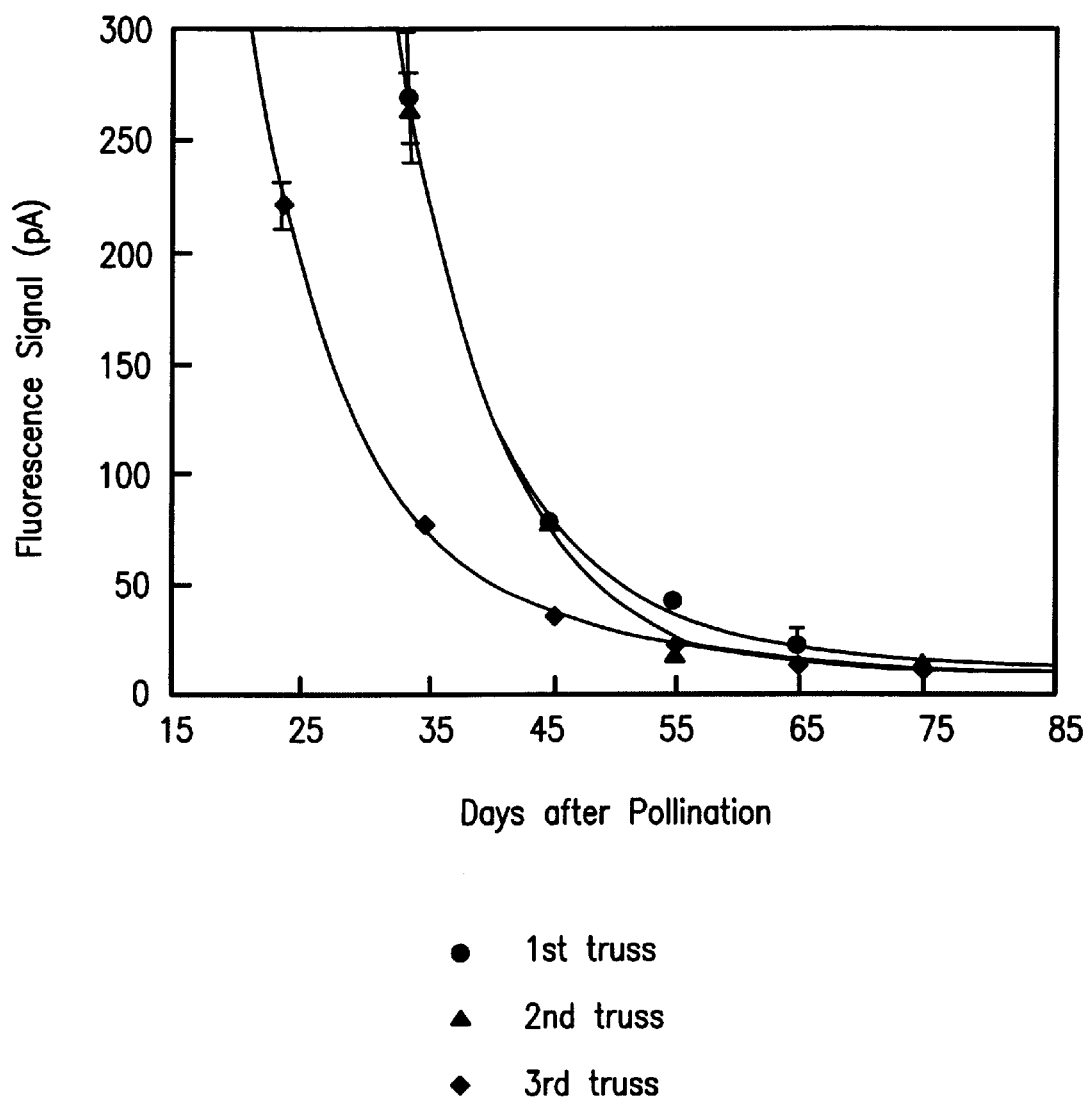
FIG. 2 shows the measurement of the chlorophyll fluorescence of tomato seeds.

In FIG. 2 the results are given of the measurement of the chlorophyll fluorescence of tomato seeds (*Lycopersicon esculentum*) cv. 'Moneymaker' supplied by R. H. Ellis, Department of Agriculture, University of Reading, Early Gate, PO Box 236, Reading RG6 2AT, UK and described by I. Demir and R. H. Ellis in "Changes in seed quality during seed development and maturation in tomato", Seed Science Research (1992) 2, 81–87. The seeds were harvested at different maturation stages, i.e. after different times of pollination. Demir et al. found that the germination of normal seedlings of the first and second truss were comparable, while the seeds of the third truss were shifted earlier in maturity by about 10 days. From the measurement of the chlorophyll fluorescence it appeared that the first and second truss gave comparable signals (FIG. 2) and thus a similar maturity at the same days after pollination. The seeds of the third truss are about 10 days ahead in maturity. This correlates well with the results obtained by Demir et al. The tomato seeds were harvested in 1989/1990, which shows that after five years the method according to the invention was still possible.

The results show that with the invention the maturity of tomato seeds could be determined and an explanation was found for the difference in germination of the tomato seeds of the first/second truss and third truss.

What is claimed is:

1. A non-destructive method for determining the maturity and quality of seeds comprising irradiating a seed with electromagnetic radiation comprising wavelengths capable of causing the photosynthetically inactive chlorophyll of the seed to fluoresce, passing the signal returning from the seed through a filter capable of filtering out the wavelengths used for exciting the chlorophyll of the seed to obtain a chlorophyll fluorescence signal and measuring said signal.

2. A method according to claim 1, wherein the irradiated electromagnetic radiation has a wavelength of about 435, 650 or 670 nm and measuring fluorescence at about 690 or 730 nm.

3. An apparatus for determining the maturity and quality of seeds, comprising a part for irradiating the seeds with electromagnetic radiation wherein the electromagnetic radiation comprises wavelengths capable of causing the photosynthetically inactive chlorophyll of the seed to fluoresce, a detector area for analyzing the signal returning from the seeds, a filter capable of filtering out the wavelengths used for exciting the chlorophyll, the signal returning from the seeds is passed through said filter to obtain a chlorophyll fluorescence signal and a means for measuring the chlorophyll fluorescence signal.

4. An apparatus for sorting seeds, comprising a feeder for the seed, a part for irradiating the seeds with electromagnetic radiation, wherein the electromagnetic radiation comprises wavelengths capable of causing the photosynthetically inactive chlorophyll of the seed to fluoresce, a detector area for analyzing the signal returning from the seeds, a separation part that works on the basis of the signal remitted from the seeds, a filter capable of filtering out the wavelengths used for exciting the chlorophyll, the signal returning from the seeds is passed through said filter to obtain a chlorophyll fluorescence signal which signal is measured in the detector area.

5. A method for sorting seeds, comprising feeding each seed individually to a irradiation area, irradiating the seed in the irradiating area with electromagnetic radiation capable of causing the photosynthetically inactive chlorophyll in the seed to fluoresce, passing the signal returning from the seed through a filter capable of filtering out the wavelengths used for exciting the chlorophyll to obtain a chlorophyll fluorescence signal and separating the seeds into classes based on their individual fluorescence signal, wherein the values that define the classes are chosen on the basis of the distribution of the chlorophyll fluorescence signals of a sample of the seeds having known properties.

* * * * *